(12) United States Patent  (10) Patent No.: US 8,532,321 B2
Parker et al.  (45) Date of Patent: Sep. 10, 2013

(54) HEARING DEVICE HAVING ONE OR MORE IN-THE-CANAL VIBRATING EXTENSIONS

(75) Inventors: John Parker, Roseville (AU); Derek Ian Darley, Cromer Heights (AU)

(73) Assignee: Cochlear Limited, Macquarie University, NSW (AU)

( * ) Notice: Subject to any disclaimer, the term of this patent is extended or adjusted under 35 U.S.C. 154(b) by 871 days.

(21) Appl. No.: 12/168,603

(22) Filed: Jul. 7, 2008

(65) Prior Publication Data

US 2009/0245556 A1 Oct. 1, 2009

Related U.S. Application Data

(60) Provisional application No. 61/041,185, filed on Mar. 31, 2008.

(51) Int. Cl.
*H04R 25/00* (2006.01)

(52) U.S. Cl.
USPC ........................................ 381/326; 29/896.21

(58) Field of Classification Search
USPC ...................................... 381/326; 29/896.21
See application file for complete search history.

(56) References Cited

U.S. PATENT DOCUMENTS

| | | | |
|---|---|---|---|
| 4,407,389 A | 10/1983 | Johnson | |
| 5,606,621 A | 2/1997 | Reiter et al. | |
| 5,781,646 A | 7/1998 | Face | |
| 6,137,889 A * | 10/2000 | Shennib et al. | 381/328 |
| 6,643,378 B2 | 11/2003 | Schumaier | |
| 6,940,989 B1 * | 9/2005 | Shennib et al. | 381/326 |
| 7,209,568 B2 | 4/2007 | Arndt et al. | |
| 7,722,524 B2 * | 5/2010 | Lupin et al. | 600/25 |
| 2002/0122563 A1 | 9/2002 | Schumaier | |
| 2002/0172386 A1 | 11/2002 | Bayer | |
| 2003/0112992 A1 | 6/2003 | Rapps | |
| 2006/0023908 A1 * | 2/2006 | Perkins et al. | 381/328 |
| 2006/0056649 A1 | 3/2006 | Schumaier | |
| 2006/0098833 A1 | 5/2006 | Juneau et al. | |
| 2006/0159297 A1 | 7/2006 | Wirola et al. | |
| 2010/0222639 A1 | 9/2010 | Purcell et al. | |

FOREIGN PATENT DOCUMENTS

| | | |
|---|---|---|
| JP | 2004-166174 A | 6/2004 |
| WO | 0193645 | 12/2001 |
| WO | 2004093401 | 10/2004 |
| WO | 2005000391 | 1/2005 |
| WO | WO 2008/014498 A2 | 1/2008 |
| WO | WO 2009/121118 A1 | 10/2009 |

OTHER PUBLICATIONS

International Application No. PCT/AU2009/000374, International Preliminary Report on Patentability mailed on Oct. 5, 2010, 7 Pages.

(Continued)

*Primary Examiner* — Eugene Lee
(74) *Attorney, Agent, or Firm* — Kilpatrick, Townsend & Stockton, LLP.

(57) ABSTRACT

A bone conduction device for enhancing the hearing of a recipient, comprising: a sound input element configured to receive an acoustic sound signal; an electronics module configured generate an electrical signal representing the acoustic sound signal; a transducer configured to generate mechanical forces representing the electrical signal for delivery to the recipient's bone; and one or more vibration extensions mechanically coupled to the transducer and configured to be inserted into the ear canal of the recipient, and further configured to vibrate in order to transmit the mechanical forces generated from the transducer to the recipient's bone.

20 Claims, 13 Drawing Sheets

(56) References Cited

OTHER PUBLICATIONS

International Application No. PCT/AU2009/000374, Written Opinion mailed on Jun. 4, 2009, 6 Pages.

International Application No. PCT/AU2009/000374, International Search Report mailed on Jun. 9, 2009, 4 Pages.

International Application No. PCT/US2007/74667, International Search Report mailed on Sep. 16, 2008, 3 Pages.

* cited by examiner

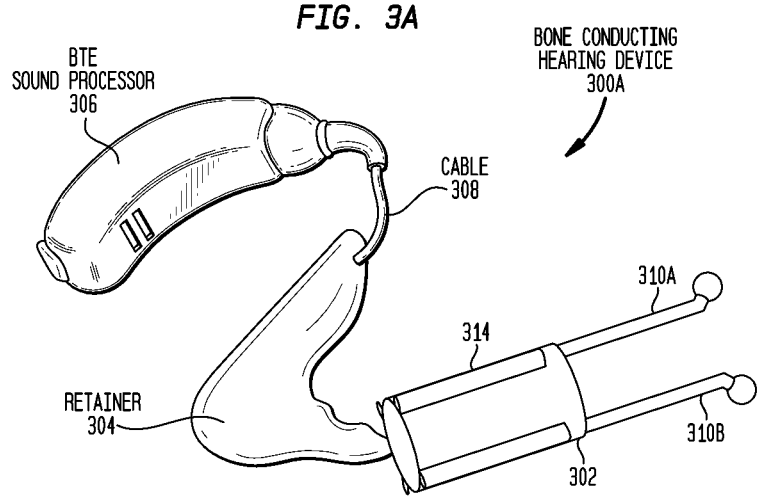

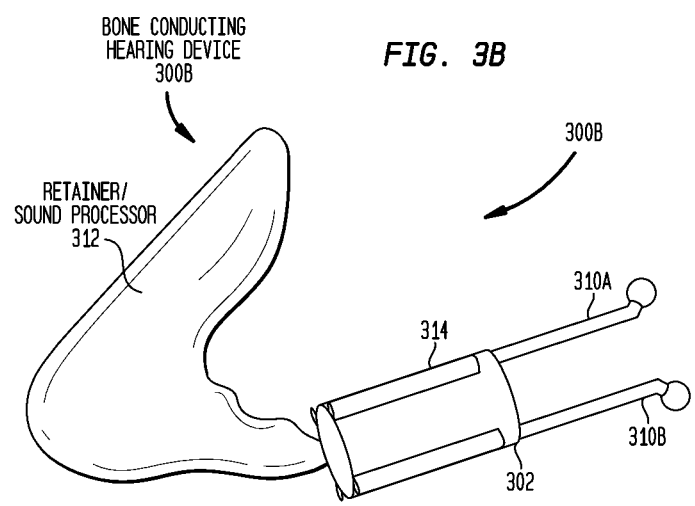

HEARING DEVICE HAVING ONE OR MORE IN-THE-CANAL VIBRATING EXTENSIONS

CROSS-REFERENCE TO RELATED APPLICATIONS

The present application claims the benefit of U.S. Provisional Patent Application 61/041,185; filed Mar. 31, 2008, which is hereby incorporated by reference herein.

BACKGROUND

1. Field of the Invention

The present invention relates generally to hearing devices and, more particularly, to a hearing device having one or more in-the-canal vibrating extensions.

2. Related Art

Hearing loss is generally of two types, conductive and sensorineural. The treatment of both of types of hearing loss has been quite different, relying on different principles to deliver sound signals to be perceived by the brain as sound.

Sensorineural hearing loss is due to the absence or destruction of the cochlear hair cells which transduce acoustic signals into auditory nerve impulses. Individuals suffering from sensorineural hearing loss are unable to derive any benefit from conventional hearing aids due to the absence of, or damage to, the natural mechanisms that transduce sound energy into auditory nerve impulses. In such cases, cochlear implants have been developed. Cochlear implants provide electrical stimulation to the auditory nerve via stimulating electrodes positioned adjacent to the auditory nerve, essentially bypassing the hair cells of the cochlea. Application of an electrical stimulation pattern to the auditory nerve endings causes impulses to be sent to the brain, resulting in sound perception.

Conductive hearing loss occurs when the normal mechanical pathways for sound to reach the hair cells in the cochlea are impeded, for example, by damage to the ossicles. In such cases, hearing loss is often improved with the use of conventional hearing aids, which amplify sound. Such hearing aids utilize acoustic mechanical stimulation, whereby the sound is amplified according to a number of varying techniques, and is delivered to the inner ear as mechanical energy. This may be through a column of air to the eardrum, or through direct delivery to the ossicles of the middle ear.

One class of hearing device, referred to as air conduction devices, delivers the mechanical energy by delivering a column of air to the eardrum. Such air conducting devices work by collecting ambient sound with a microphone, amplifying the sound and delivering the amplified signal by way of a speaker positioned in the outer portion of the ear canal.

Another class of device, referred to as middle ear implants, delivers the mechanical energy by directly delivering the mechanical energy to the ossicles of the middle ear. Such middle ear implants work by collecting ambient sound with a microphone, processing the sound and vibrating a rod implanted adjacent to or fixed to a bone in the ossicular chain, or adjacent the oval window of the cochlea.

A further class of device, referred to as a bone anchored hearing aid, converts incoming sound into mechanical vibrations that are transmitted through the bone surrounding the otic capsule. The resulting bone vibrations stimulate the cochlea, resulting in a perceived sound. The direct bone conduction provided by a bone anchored hearing aid has been utilized as a treatment for conductive and mixed hearing losses (with a mild sensoneural component) as well as for the treatment of unilateral sensorineural hearing loss. Typically, a bone anchored hearing aid is used to help people with chronic ear infections, congenital external auditory canal atresia and single sided deafness, as such persons often cannot benefit from conventional hearing aids. Conventional bone anchored hearing aid devices are surgically implanted to allow sound to be conducted through the bone rather than via the middle ear.

SUMMARY

A bone conduction device for enhancing the hearing of a recipient, comprising: a sound input element configured to receive an acoustic sound signal; an electronics module configured generate an electrical signal representing the acoustic sound signal; a transducer configured to generate mechanical forces representing the electrical signal for delivery to the recipient's bone; and one or more vibration extensions mechanically coupled to the transducer and configured to be inserted into the ear canal of the recipient, and further configured to vibrate in order to transmit the mechanical forces generated from the transducer to the recipient's bone.

A method for rehabilitating the hearing of a recipient with a bone conduction device having one or more vibration extensions, mechanically coupled to a transducer, and configured to be inserted into the ear canal of the recipient, comprising: receiving an electrical signal representative of an acoustic sound signal; generating mechanical forces representative of the received electrical signal; contacting the ear canal of the recipient with the one or more vibration extensions; and delivering the mechanical forces to the recipient's skull.

A device for rehabilitating the hearing of a recipient with a bone conduction device having one or more vibration extensions, comprising: means for receiving an electrical signal representative of an acoustic sound signal; means for generating mechanical forces representative of the received electrical signal; means for contacting the ear canal of the recipient with the one or more vibration extensions; and means for delivering the mechanical forces to the recipient's skull.

BRIEF DESCRIPTION OF THE DRAWINGS

Embodiments of the present invention will be described below with reference to the attached drawings, in which:

FIG. 3A is a perspective view of a bone conduction hearing device in accordance with one embodiment of the present invention;

FIG. 3B is a perspective view of the bone conduction hearing device, in accordance with an alternative embodiment of the present invention;

DETAILED DESCRIPTION

Aspects of the present invention are generally directed to a self-retaining bone conduction hearing device having one or more in-the-canal vibrating extensions configured for non-surgical-implantation in a recipient's ear canal.

Unlike conventional hearing devices having an in-the-canal component, the hearing device of the present invention does not require surgical implantation of a bone conduction element such as a post or anchor. Furthermore, the device of the present invention does not interrupt the ossicular chain. In other words, the present invention does not interfere with the recipient's remaining natural hearing. Still further, in certain embodiments of the present invention, the external auditory canal is not occluded, thus permitting the normal biological functioning of the ear. For example, the present invention facilitates the normal egress of cerumen (ear wax) and the normal circulation of air and other fluids, thereby reducing the likelihood of external ear infections, allergic response and intolerance.

The human auditory system includes the outer ear, the middle ear and the inner ear. In a fully functional ear, the outer ear comprises an auricle or pinna and an ear canal. An acoustic pressure or sound wave is collected by the auricle and channeled into and through the ear canal. Disposed across the distal end of the ear canal is a tympanic membrane which vibrates in response to acoustic wave. This vibration is coupled to the oval window of the cochlea through three bones of the middle ear, collectively referred to as the ossicles or ossicular chain. The ossicles serve to filter and amplify the acoustic wave, causing the oval window to vibrate. Such vibration sets up waves of fluid motion within the cochlea. Such fluid motion, in turn, activates tiny hair cells that line the inside of the cochlea. Activation of the hair cells causes appropriate nerve impulses to be transferred through the spiral ganglion cells and auditory nerve to the brain, where they are perceived as sound.

Figure 1:
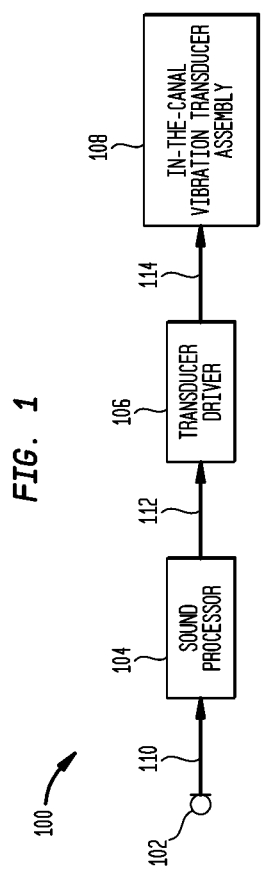
FIG. 1 is a high-level functional block diagram of a bone conduction hearing device having an in-the-ear vibration transducer assembly, in accordance with one embodiment of the present invention.

Embodiments of the present invention are described next below with reference to a functional block diagram in FIG. 1. Then, the human outer ear is described in greater detail with reference to FIG. 2. Thereafter, the invention will be described with reference to FIGS. 3-8 illustrating examples of how the functional components described in FIG. 1 may be implemented.

As noted, aspects of the present invention are directed to a self-retaining bone conduction hearing device having a vibrating component configured for non-surgical-implantation in a recipient's ear canal. FIG. 1 is a high-level functional block diagram of a bone conduction hearing device in which the one or more in-the-canal vibrating extensions is a passive device; that is, it does not contain a transducer. Hearing device 100 comprises a microphone 102 that converts received ambient sound to electrical signals 104 representative of the received sound. Microphone 102 may be a traditional miniature hearing aid microphone, and is preferably flexibly mounted to minimize the impact of shock and to resist pickup of extraneous noise. More than one microphone, for example, an array of microphones, may be employed in alternative embodiments. Multiple microphones may allow selectable modes of sound reception, for example, speech focused in front of the user versus multi-directional sound. Sounds sensed through microphone 102 may be transduced by the microphone into electrical signals 110 for sound processor 104.

Sound processor 104 processes electrical signals 110 to generate output signals 112. In one embodiment, sound processor 104 may amplify, filter, and optimize the sound information received from microphone 102 in analog or digital form. Sound processor 104 may further convert the information into a format suitable for transmission to transducer driver 106. Sound processor 104 may optionally contain control circuits accessible via a user interface. Such an interface provides user control to certain parameters associated with the operation of hearing device 100, such as the amplitude of the bone vibrations, or the frequencies of the signals (that is, tone control) that are to be processed. As such, the user interface may include an on/off switch, a volume control, capability to switch between various sound processing programs or hearing profiles (e.g., via a knob), an indicator of remaining power, and the like.

Any type of signal processing (a.k.a. sound processing) may be employed, as is known in the hearing aid art (for example, different frequency responses), in order to enhance the ability of the recipient to benefit from the sound amplification. Different signal processing strategies may be selected through the user interface, and may be modified, from time to time, as needed or desired.

Sound processor 104 is configured to exchange information with an external programming unit to allow an audiologist or clinician to initially program or "fit" hearing device 100 with a customized hearing profile(s), or make programming adjustments after some amount of use, so that it optimally meets the needs and preferences of the recipient. Fitting may include adjusting hearing device 100 to utilize a desired frequency response or signal processing strategy.

Preferably, sound processor 104 may also accept direct input from commercial electronics devices, such as telephones (land line or cellular network such as USTM network), computers, personal digital assistants, televisions, DVD players, CD players, AM/FM and/or two way radios, and the like.

Sound processor 104 sends vibration commands 112 to vibration transducer assembly 108 via a transducer driver 106. Transducer driver 106 converts commands 112 to an appropriate form and format 114 suitable for the particular embodiment of in-the-canal vibration transducer assembly 108. Transducer driver 106 transmits drive signals 114 to a vibration transducer 108. Vibration transducer assembly 108, which is securely placed (implanted is not the appropriate word) in a recipient's ear canal, transduces the sound information to physical movement in the form of vibrations. Vibration transducer assembly 108 vibrates in a manner that the sound information is provided to the recipient's auditory nerve via bone conduction through the recipient's bone.

Figure 2:
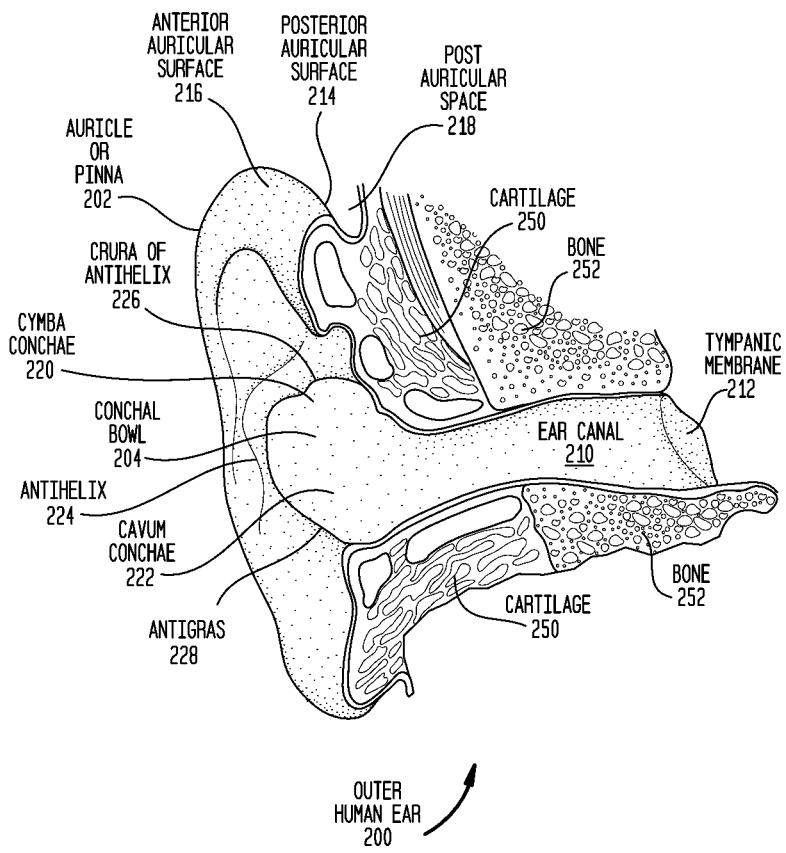
FIG. 2 is a partial cross-sectional view of a human auditory system.

FIG. 2 is a side and cross-sectional view of the outer ear 200 of a human recipient. Outer ear 200 comprises the auricle or pinna 202 and an ear canal 210. An acoustic pressure or sound wave is collected by auricle 202 and channeled into and through ear canal 210 to vibrate tympanic membrane 212 disposed across the distal end of ear canal 210.

A posterior surface 214 of auricle 202 is spaced from the recipient's bone forming a post-auricular space 218. The anterior surface 216 of auricle 202 comprises a variety of features for facilitating the channeling of sound waves into ear canal 210. Relevant features include the raised ridge formed by the crura of antihelix 226, antihelix 224, and antigras 228, which form a perimeter of conchal bowl 204. Conchal bowl 204 comprises cymba conchae 220 and cavum conchae 222.

Exemplary implementations of hearing device 100 are described next below with reference to FIGS. 3A-3C. First, FIGS. 3A-3C are described followed by a detailed description of the components of the hearing devices illustrated in FIGS. 3A-3C.

FIG. 3A is a perspective view of a bone conducting hearing device 300A comprising a behind-the-ear sound processor 306 and an in-the-canal vibrating component 302 having one or more vibrating extensions 310A and 310B (collectively referred to herein as vibrating extensions 310). A retainer 304 is secured to the proximal end of vibrating component 302. Sound processor 306 controls vibrating component 302 via a cable 608 which is passed through retainer 604. Hearing device 300A may be positioned in outer ear 200 of a recipient. Behind-the-ear sound processor 306 is positioned in post-auricular space 218. Retainer 304 is configured to be self-retained in conchal bowl 204 and, more specifically, in cymba conchae 220 of conchal bowl 204. Vibrating element 302 is configured to be implanted in ear canal 210, and comprises one or more spacers 314 to permit the passage of bodily fluids and sound. Thus, vibrating component 602 is referred to herein as an in-the-ear vibrating component.

FIG. 3B is a perspective view of a bone conducting hearing device 300B comprising a in-the-canal vibrating component 302, as introduced above, having one or more vibrating extensions 310A and 310B (collectively referred to herein as vibrating extensions 310). A retainer/sound processor 312 is secured to the proximal end of vibrating component 302. Retainer/sound processor 312 is configured to be self-retained in conchal bowl 204. More specifically, retainer/sound processor 312 is configured to be self-retained in cymba conchae 220 and cavum conchae 222. Device 300B comprises one or more spacers 314 to permit the passage of bodily fluids and sound.

Figure 3C:
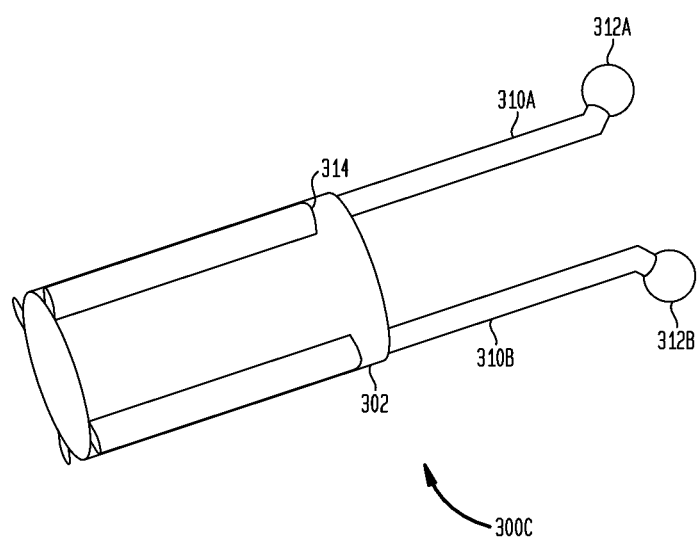
FIG. 3C is a perspective view of the bone conduction hearing device, in accordance with an alternative embodiment of the present invention.

FIG. 3C is a perspective view of a bone conducting hearing device 300C comprising a free-standing in-the-canal vibrating component 302, as introduced above, having one or more vibrating extensions 310A and 310B (collectively referred to herein as vibrating extensions 310). In the embodiment of the present invention illustrated in FIG. 3C, vibrating extensions 310 comprises contact points 312A and 312B on each of the ends of vibrating extensions 310A and 310B, respectively. Furthermore, device 300C comprises one or more spacers 314 to permit the passage of bodily fluids and sound, as described previously. In operation, in-the-canal vibrating component 302 comprises a sound processor, a microphone (not shown), and other electronic components necessary to detect and process sound stimulation and further generate and transmit vibrations representative of that processed sounds through vibrating extensions 310.

Turning now to the components of hearing devices 300A, in-the-canal vibrating component 302 is configured to be placed in the ear canal 210 to provide vibrations to cartilage 250 and, perhaps, bone 252. The term vibrating component refers to any embodiment of an in-the-canal component that delivers vibrations to the recipient in response to commands generated by a sound processor. In certain embodiments of the present invention, vibrating component 302 is non-occluding. That is, there are one or more spacers 314 that permit the passage of bodily fluids and sound. As such, embodiments of the present invention are particularly useful for use in recipients having conductive hearing loss and excessive drainage. In contrast to conventional approaches in which such drainage are plugged by traditional acoustic hearing aids, embodiments of the present invention allow drainage through pass past spacers 314. This also alleviates the effects of having an occlusion totally obstructing the ear canal, such as exacerbated drainage and lack of ventilation. Furthermore, in certain embodiments of the present invention, vibrating component 302 comprises a motor which converts electrical signals into mechanical force. In one embodiment, a transducer may be used in conjunction with the present invention to convert the electrical signals into a mechanical motion or force. One example of a transducer which may be suited for use in the present invention is a piezoelectric element that deforms in response to application of the electrical signal thereto.

The piezoelectric element converts an electrical signal applied thereto into a mechanical deformation (i.e. expansion or contraction) of the element. The amount of deformation of a piezoelectric element in response to an applied electrical signal depends on material properties of the element, orientation of the electric field with respect to the polarization direction of the element, geometry of the element, etc. The bone conduction device generates a mechanical force that is delivered to the bone, thereby causing motion of the cochlea fluid and a hearing perception by the recipient.

The non-occluding aspect of vibrating component 302 leaves ear canal 210 open thereby avoiding the occlusion effect (the wearer's own voice sounds altered to themselves because of closing the ear canal accentuates the low frequencies heard in the voice) commonly provided by conventional hearing aids. Other key advantages of having ear canal 210 open are that the recipient may hear ambient sounds making the recipient more aware of his/her environment.

In the embodiment of vibrating component 302 illustrated in FIG. 3A and described elsewhere herein, vibrating component 302 has four spacers 314 disposed radially around component 302. It should be appreciated, however, that in alternative embodiments, vibrating component 302 may comprise more or less numbers of spacers 314 disposed along the substantial longitudinal length of component 302 or, alternatively, only for a portion of the longitudinal length of component 302. Furthermore, for a single embodiment of the present invention, all spacers 314 may have uniform dimensions with respect to one another. Alternatively, spacers 314 may have different dimensions with respect to each other, depending on the intended position within ear canal 210.

Alternative arrangement is to have the mechanical assembly fitted like an ear mould around so that this is a snug fit and the hole pass through the centre. The support doesn't have to position the transducer radially at the center.

In the embodiments described herein, vibrating component 302 has a uniform cross-section. It should also be appreciated, however, that vibrating component 302 may have other cross-sectional shapes that provide one or more of the above-noted benefits associated with a non-occluding vibrating component. For example, in one embodiment, vibrating component 302 is ovoid. In another embodiment, vibrating component 302 is rectangular with rounded corners.

As noted, hearing device 300A comprises a retainer 304 configured to be self-retained in cymba conchae 210 of conchal bowl 204, and hearing device 300B comprises a retainer/sound processor 312 configured to be self-retained in cymba conchae 210 and cavum conchae 222 of conchal bowl 204. Retainers 304 contribute to the long-term retention of vibrating component 302 in ear canal 210. If necessary or desired, retainer 312 may be implemented to further contribute to the retention of vibrating component 602. It should be appreciated that such retention may also be aided by a postauricular extension such as behind-the-ear sound processor 306.

The materials that retainers 304, 312 are made of hypoallergenic material. In certain embodiments one or both retainers 304, 312 are formed of Lucite or Silicone. Retainers 304, 312 may be molded from one of the materials used in traditional hearing aid molds. These materials are classified broadly into hard and soft or flexible materials. All such materials allow a snug, comfortable fit in ear canal 210, are easy to clean and remain stable without exciting an inflammatory tissue reaction (hypoallergenic).

Possible hard mold materials include acrylic resin. This material is inert and hypoallergenic. It does not distort with moisture and temperature changes and can be easily ground to make modifications to its shape. Flexible materials include soft acrylic, plastics and silicon. Soft acrylic moulds show some deformation with increased temperatures making them less suitable for hot climates. Plastics including vinyl and polypropylene are more stable, but they tend to shrink and harden with time and typically require replacement after 18-24 months. Silicon polymer moulds such as MDX (peroxide catalysed) are comfortable and inert.

Preferably, all molds will be custom fit to the individual ear canal 210. This procedure is quick, painless, easy to perform and uses a well-established technique familiar to all hearing aid technicians. A soft foam plug is placed into the ear canal before soft silicon putty is injected and allowed to set. The impression is removed a few minutes later and can be used to make a more durable mould. The finished mould may then be canalized and the transducer inserted.

Retainers 304, 312 retain hearing device 300A, 300B in their operable position on the recipient without additional support and without surgical implantation. It should be appreciated, however, that this self-retaining feature of the bone conducting hearing device of the present invention may be provided by one or more components of the device. For example, in one embodiment, the in-the-ear component 302 is snugly fit within ear canal 210. In other embodiments, other components are configured to compliment the self-retaining function performed by the in-the ear component. For example, in one embodiment, passive molded retainer 304 is configured to snugly fit within conchal bowl 204 of the recipient. In a further embodiment, the connection of the in-the-ear component 302 with the behind-the-ear (BTE) component 306 residing in post-auricular space 218 further contributes to the self-retaining characteristic of the device. As one of ordinary skill in the art would appreciate, any combination of one or more of these or other features may be implemented in a hearing aid device to attain a desired or required degree of self-retention. This may be a function of, for example, the type of transducer, the mass of the device and the activity level of the recipient, among other factors.

It should also be appreciated that other techniques may be utilized to attain a desired degree of self-retention. For example, in one embodiment, piercing is utilized additionally or alternatively to the techniques described above. In another embodiment, the device may be retained by an elastic cloth covering the whole pinna and ear, which retains the device in place in the ear canal.

Behind-the-ear sound processor 306 is any sound processor now or later developed such as sound processor 104.

As noted above with reference to FIGS. 3A-3C, vibrating component 302 may comprise in-the-ear canal vibration transducer assembly 108 and operates to transfer vibrations to the recipient's bone.

Figure 4:
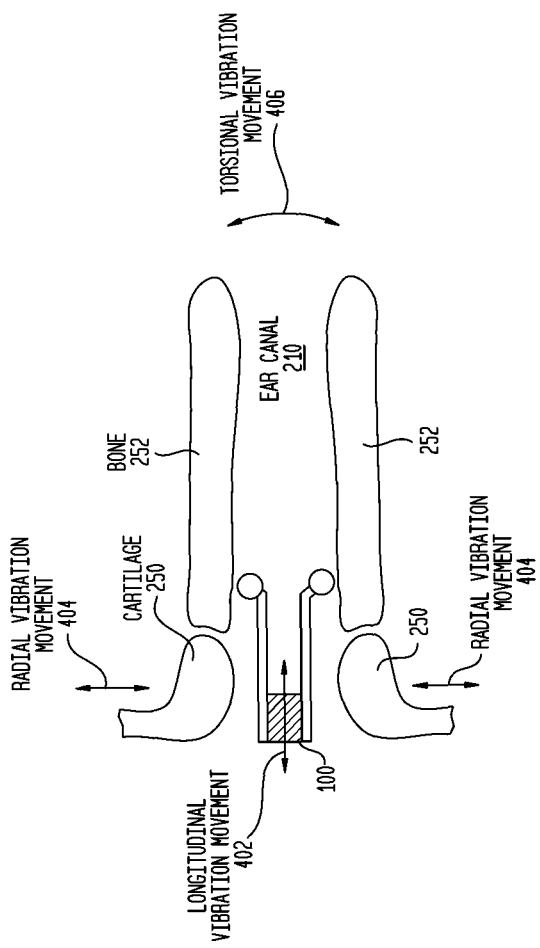
FIG. 4 is a schematic diagram showing the direction of movement which may be implemented in various embodiments of the one or more in-the-canal vibrating extensions of the present invention.

Different embodiments of vibrating component 302 may vibrate; that is, move, in different directions. This is referred to herein as the vibration mode of vibrating component 302. FIG. 4 is a schematic diagram of bone conducting hearing devices 300A, 300B, 300C implanted in a recipient's ear, also shown schematically. In this representative environment, vibrating component 302 extends past cartilaginous ear canal 250 into a portion of bony ear canal 252. It should be appreciated, however, that different depths of implantation may be implemented in connection with different vibrating modes to achieve a desired result.

Three different vibration modes are illustrated in FIG. 4. Radial vibration movement 404 occurs when vibrating extensions 310 of vibrating component 302 expands and contracts. Longitudinal vibration movement 302 occurs when vibrating component 302 moves in and out of ear canal 210. And, torsional vibration movement 406 occurs when vibrating component 302 rotates or twists.

Different vibration modes 402, 404, 406 may be implemented to attain a desired or optimal transfer of sound information. For example, certain vibration modes at certain locations in ear canal 210 may optimally deliver certain frequencies or amplitudes. Such vibration modes 402, 404, 406 may be implemented in parallel in separately-controlled portions of vibrating component 602. It should be appreciated that torsional vibration movement 406 and longitudinal vibration movement 402 may impart shear stress to the epithelium of ear canal 210.

In the exemplary embodiment illustrated in FIGS. 3A through 3C, vibration transducer assembly 108 comprises an in-the-ear vibrating component 302 which, in FIGS. 3A-3C, has been configured and arranged to fit within ear canal 210. As described in detail next below, embodiments of vibration component 302, introduced above as vibration transducer assembly 108 may comprise one or more transducers and may take on a number of configurations.

Figure 5:
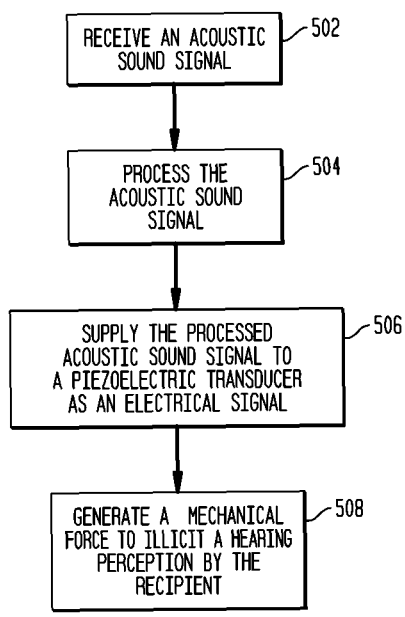
FIG. 5 is a is a flowchart illustrating the conversion of an input sound into bone vibration in a transcutaneous bone conduction hearing device according to one embodiment of the present invention.

FIG. 5 depicts a flowchart illustrating the conversion of an input acoustic sound signal into a mechanical force for delivery to the recipient's bone in accordance with embodiments of bone conduction hearing device 100. At block 502, bone conduction device 100 receives an acoustic sound signal. In certain embodiments, the acoustic sound signal is received via microphones. In other embodiments, the input sound is received via an electrical input. In still other embodiments, a telecoil integrated in, or connected to, bone conduction device 100 may be used to receive the acoustic sound signal.

At block 504, the acoustic sound signal received by bone conduction device 100 is processed by the speech processor in electronics module 204. As explained above, the speech processor may be similar to speech processors used in acoustic hearing aids. In such embodiments, speech processor may selectively amplify, filter and/or modify acoustic sound signal. For example, speech processor may be used to eliminate background or other unwanted noise signals received by bone conduction device 100.

At block 506, the processed sound signal is provided to transducer 206 as an electrical signal. At block 508, transducer 206 converts the electrical signal into a mechanical force configured to be delivered to the recipient's bone via anchor system 208 so as to illicit a hearing perception of the acoustic sound signal.

Figure 6A:
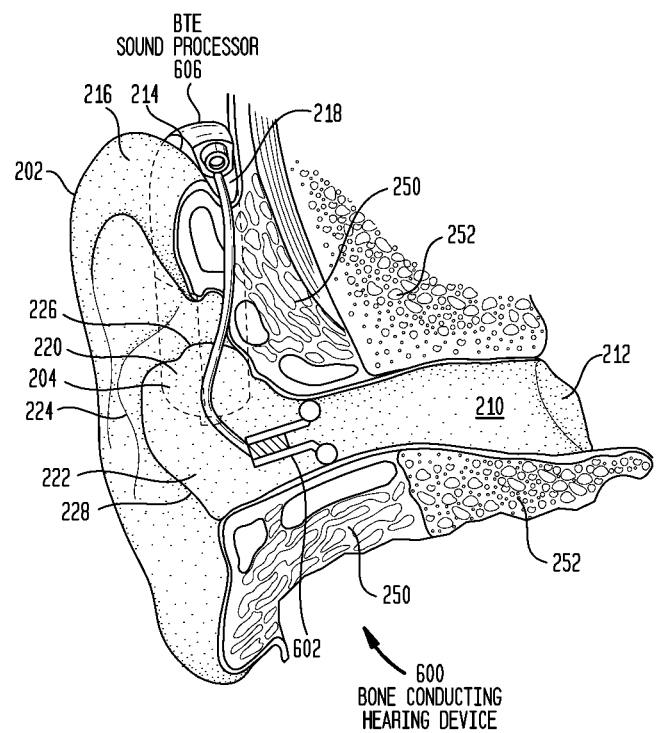
FIG. 6A is a perspective view of a bone conduction hearing device in accordance with one embodiment of the present invention.
Figure 6B:
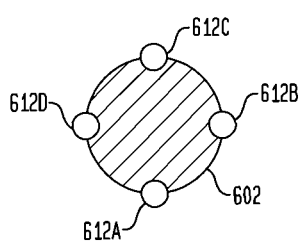
FIGS. 6B-6E are perspective views from one end of a bone conduction hearing device in accordance with various other embodiments of the present invention.
Figure 6C:
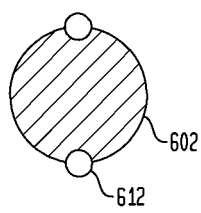

FIG. 6A is a perspective view of an alternative embodiment of the bone conducting hearing device of the present invention, referred to herein as hearing device 600. Hearing device 600 comprises an in-the-canal vibrating component 602 coupled to sound processor 606 by a cable. In one embodiment of the present invention, transducer driver 106 may be housed in the same housing as sound processor 606, providing electrical command signals to vibrating component 602. In other embodiments of the present invention, transducer driver 106 may be housed in the same housing as vibrating component 602, such as signal representing detected and processed sounds, as described earlier, are received by vibrating component 602 and further processed to generate vibrations which will represent the detected sounds to the auditory system of the recipient. Although not depicted in FIG. 6A, as described above, vibrating component 602 comprises spacers (not shown) which maintains a space through the longitudinal length of vibrating component 602 to permit air and other fluid to ingress and/or egress through ear canal 210.

FIGS. 6B-6G show various embodiments of the present invention. In FIG. 6B-6E, vibrating component 602 may comprise one or more vibrating extensions 612. For example, in the embodiment illustrated in FIG. 6B, four vibrating extensions and associated contact points 612A-612B are disposed around vibrating component 602. In the embodiment illustrated in FIG. 6C, there are two such vibrating extensions and contact points 612.

Figure 6D:
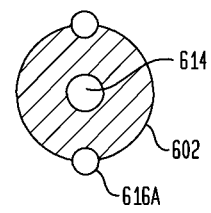
Figure 6E:
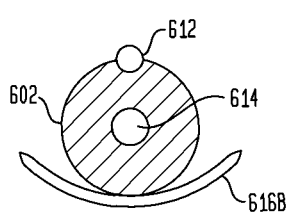
Figure 6F:
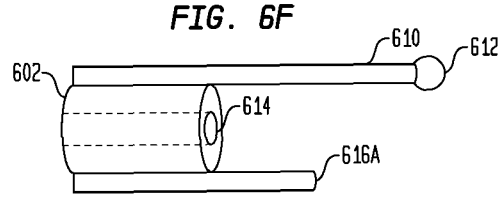
FIG. 6F is a perspective view of a bone conduction hearing device in accordance with a still further embodiment of the present invention.

In the embodiment illustrated in FIGS. 6D and 6F, an aperture 614 is disposed throughout the longitudinal length of vibrating component 602, providing the benefits as described previously with regard to permitting air and fluid flow to and from the inner ear. In the embodiment of the present invention illustrated in FIGS. 6D and 6F, a single vibrating extension having contact point 612 is disposed on vibrating component 602. A non-vibrating support arm 616A extends into the cochlear for a given length to provide a base which will exert an opposing force as vibrating extension 610 is vibrated.

Figure 6G:
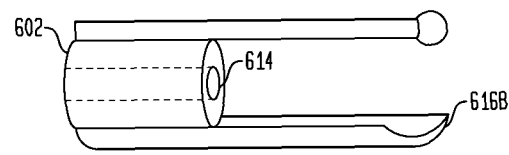
FIG. 6G is a perspective view of a bone conduction hearing device in accordance with another embodiment of the present invention.

As with the embodiment illustrated in FIGS. 6D and 6F, the embodiment illustrated in FIGS. 6E and 6G also comprise an aperture 614 disposed along its longitudinal lengths. In these embodiments, a non-vibrating support base 616B wraps around a portion of the circumference of vibrating component 602 and has a more substantial surface area than, for example, support arm 616A illustrated in FIGS. 6D and 6F. Support base 616B may be flexible in a radial direction yet, when put into a semi-cylindrical configuration, provide a rigid and inflexible support base when forces that are orthogonal to the longitudinal axis of vibrating component 602 are applied. In the embodiment illustrated in FIGS. 6E and 6G, vibrations from vibrating component 602 are directed to vibrating extension 610, such that the recipient's bones that are in direct or indirect contact with vibrating extension 610 are vibrated.

Figure 7A:
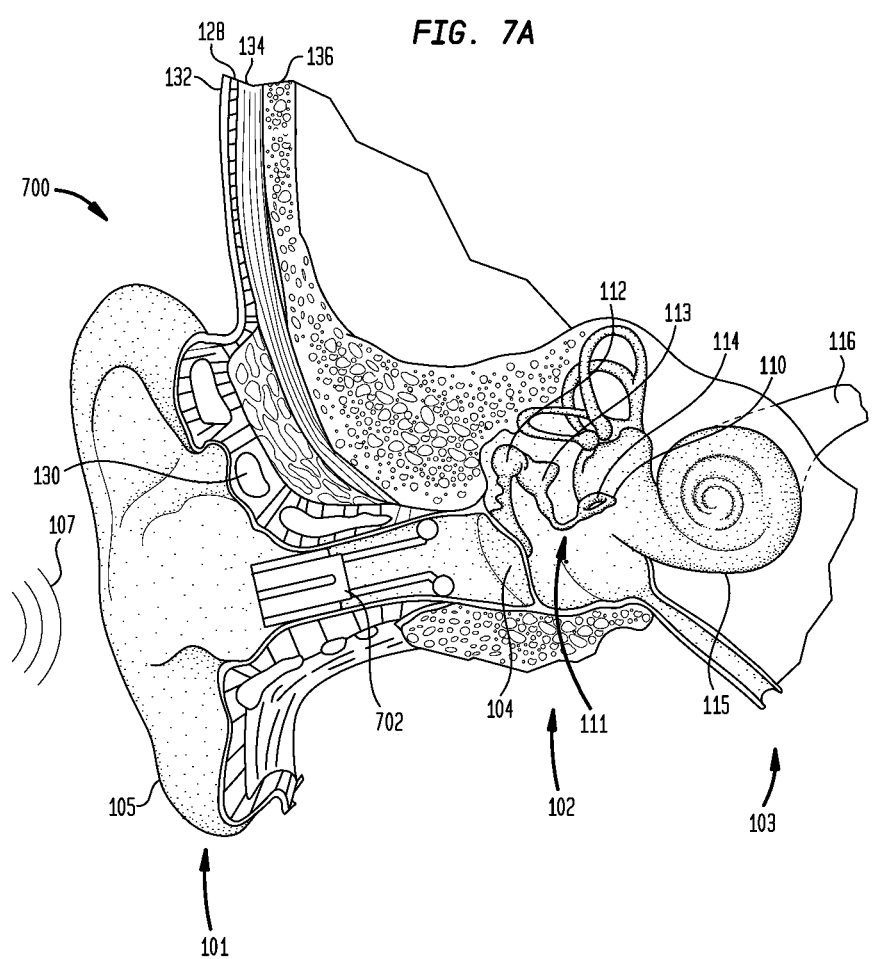
FIG. 7A is a perspective view of a bone conduction hearing device in accordance with a further embodiment of the present invention.

FIG. 7A illustrates an alternative embodiment of the present invention in which a bone conducting hearing device 100, depicted here as bone conducting hearing device 700, comprises a free-standing vibrating component 702 which, as previously described in conjunction with FIG. 3C, comprises sound processor (not shown), microphone (not shown) and other circuitry with the same housing as transducer driver 106 which generates mechanical vibration to represent the detected and processed sounds.

Figure 7B:
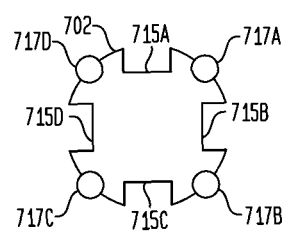
FIGS. 7B-7E are perspective views from one end of a bone conduction hearing device in accordance with various other embodiments of the present invention.
Figure 7C:
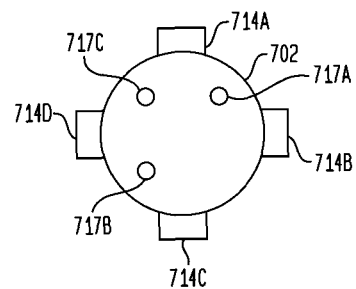
Figure 7D:
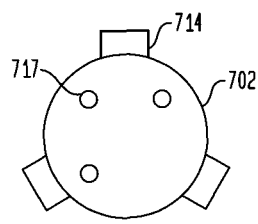
Figure 7E:
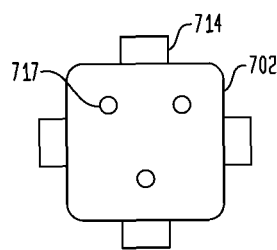
Figure 7F:
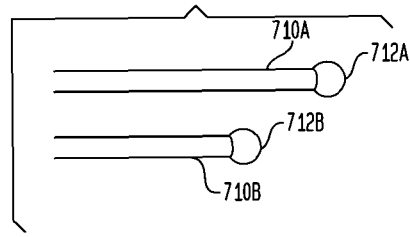
FIGS. 7F-7J are perspective views of one or more extensions of a bone conduction hearing device in accordance with various other embodiments of the present invention.
Figure 7G:
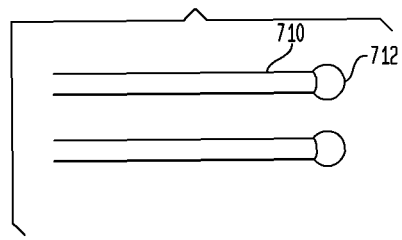

As illustrated in FIGS. 7C-7E, vibrating component 702 may comprise spacers 714A, 714B, 714C, 714D (collectively referred to as spacers 714) to maintain a gap between ear canal 210 and vibrating component 702 along its longitudinal length. Additionally or alternatively, in other embodiments of the present invention as illustrated in FIG. 7B, one or more recesses 715A, 715B, 715C, 715D (collectively referred to as recesses 715) may be disposed along the longitudinal length of vibrating components to similarly provide or maintain a gap between ear canal 210 and vibrating component 702 along its longitudinal length. Furthermore, as illustrated in FIGS. 7B-7E, user interfaces 717A, 717B, 717C, 717D (collectively referred to as interfaces 717) or other mechanisms such as user buttons, now known or later developed, may be disposed at the end of vibrating component closer to the outside environment such that the recipient or a third party may access the buttons or other interface. For example, in one embodiment of the present invention, user interface 717A is a button which, when pressed, causes the output generated by vibrating component 702 to be increased in magnitude such that the volume perceived by the recipient is increased. In this embodiment, another user interface 717B is a button which, when pressed, causes the output generated by vibrating component 702 to be decreased in magnitude such that the volume perceived by the recipient is decreased.

Figure 7H:
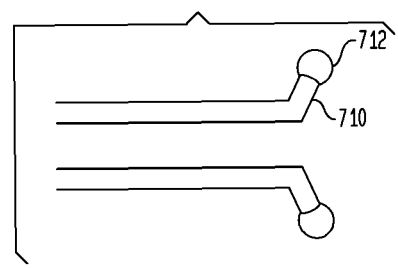
Figure 7I:
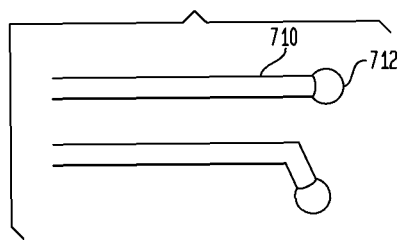
Figure 7J:
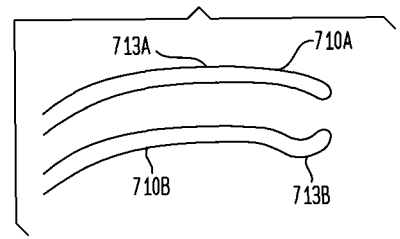

FIGS. 7F-7J illustrates various vibrating extensions 710A and 710B (collectively referred to as vibrating extensions 710) according to various embodiments of the present invention. As noted previously, vibrating extensions 710 may comprise one or more extensions. For example, in the embodiment illustrated in FIG. 7F, there are two vibrating substantially straight extensions 710 which are of disparate lengths. In the embodiment illustrated in FIG. 7G, two straight vibrating extensions 710 are of substantially equal length. As illustrated in FIG. 7H, vibrating extensions 710 may be substantially straight for the majority of its length before bending towards ear canal 210, thus allowing the two vibrating extensions to be close to each other for the majority of their lengths. As illustrated in FIG. 7I, in one embodiment of the present invention, one or more vibrating extensions 710 may be straight while other vibrating extensions 710 may be bent at some point along their length. Finally, as illustrated in FIG. 7J, while other embodiments illustrated in FIGS. 7F-7I also comprised contact points 712A and 712B (collectively referred to as contact points 712), in other embodiments of the present invention, vibrating extensions 710 may be configured such that vibrating extensions 710 makes contact with ear canal 210 at some point along the length of vibrating extensions 710, for example at contact points 713A and 713B, instead of at the ends of vibrating extensions 710. By designing vibrating extensions 713A and 713B to make contact with ear canal 210 at some point along their lengths, a single design may accommodate the varying sizes and dimensions of a multitude of recipients. For example, in the embodiment illustrated in FIG. 7J, with regard to vibrating extension 710A, some recipients' ear canals may make contact with contact point 713A at the middle of vibrating extension 710A, while other recipients' ear canals may make contact with contact point 713A closer to the end of vibrating extension 710A.

Figure 8:
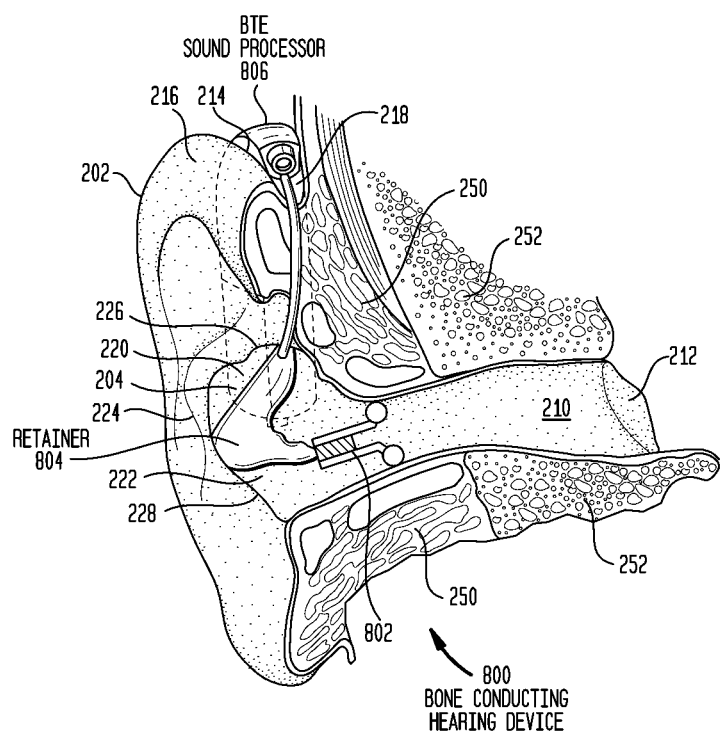
FIG. 8 is a perspective view of a bone conduction hearing device in accordance with a further embodiment of the present invention.

In the embodiment illustrated in FIG. 8, vibrating component 802 implanted in a recipient's ear canal 210 is located only within cartilaginous ear canal 250, and does not enter or physically contact bony ear canal 252. It is understood, however, that vibrating component 802 may be successfully implemented as a component of a bone conducting hearing device due to the intimate and tight connection between cartilage 250 of ear canal 210 and adjacent bone 252.

As noted, vibrating component 802 is implanted in ear canal 210. However, the size of ear canal 210 varies among potential recipients. This may be due to, for example, surgical modification or physiological variations. Customization of the size of vibrating components 802 is preferable to optimize mechanical coupling to ear canal 210. Proper sizing of vibrating component 802 also improves comfort and avoids trauma to the epithelium of ear canal 210.

As noted above, vibrating component 802 may be customized to the ear canal 210 of the recipient by over-molding the vibrating element 108. Such over-molding may be performed using standard hearing aid custom molding techniques. It should be appreciated, however, that such over-molding is just one approach to ensuring vibrating components 802 are optimally fitted to a particular ear canal 210. Embodiments of vibrating components 802 which are adjustable in size may be implemented in addition to, or alternatively to, over-molding.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom. For example, throughout the above descriptions, a microphone 102 has been referenced. It should be appreciated, however, that a sound pick-up device now or later developed may be used, and that such devices are considered to be included in the definition of the term "microphone." As another example, in certain embodiments the two prongs could be made to be adjustable in separation. The amount of force which is applied to the inside of the ear canal is critical for comfort. The tynes of the two prongs could be sprung loaded however there will likely be losses associated with transmitting sound through the springs. Alternatively the tynes could be made adjustable and have some form of active adjustment incorporate therein.

All documents, patents, journal articles and other materials cited in the present application are hereby incorporated by reference.

What is claimed is:

1. A bone conduction device for enhancing the hearing of a recipient, comprising:
    a sound input element configured to receive an acoustic sound signal;
    an electronics module configured generate an electrical signal representing said acoustic sound signal;
    a transducer configured to generate mechanical forces representing said electrical signal for delivery to the recipient's bone; and
    one or more vibration extensions mechanically coupled to said transducer and configured to be inserted into the ear canal of the recipient and contact the recipient's ear canal at their respective ends, and further configured to vibrate in order to transmit said mechanical forces generated from said transducer to the recipient's bone.

2. The device of claim 1, wherein said transducer comprises a piezoelectric element configured to generate vibration forces.

3. The device of claim 1, further comprising:
    one or more spacers disposed around the circumference of said transducer and configured to allow fluidic access through the recipient's ear canal.

4. The device of claim 1, wherein the electronics module is directly coupled to the transducer by a cable.

5. A bone conduction device for enhancing the hearing of a recipient, comprising:
    a sound input element configured to receive an acoustic sound signal;
    an electronics module configured generate an electrical signal representing said acoustic sound signal;
    a transducer configured to generate mechanical forces representing said electrical signal for delivery to the recipient's bone; and
    one or more vibration extensions mechanically coupled to said transducer and configured to be inserted into the ear canal of the recipient and contact the recipient's ear canal at a point prior to their respective ends, and further configured to vibrate in order to transmit said mechanical forces generated from said transducer to the recipient's bone.

6. The device of claim 5, wherein said electronics module and said transducer are disposed in a common housing.

7. The device of claim 6, wherein said common housing is configured to be inserted into the recipient's ear canal.

8. A bone conduction device for enhancing the hearing of a recipient, comprising:
    a sound input element configured to receive an acoustic sound signal;
    an electronics module configured generate an electrical signal representing said acoustic sound signal;
    a transducer configured to generate mechanical forces representing said electrical signal for delivery to the recipient's bone, wherein said transducer has disposed along its longitudinal axis an aperture which is configured to allow fluidic access through the recipient's ear canal; and
    one or more vibration extensions mechanically coupled to said transducer and configured to be inserted into the ear canal of the recipient, and further configured to vibrate in order to transmit said mechanical forces generated from said transducer to the recipient's bone.

9. The device of claim 8, further comprising:
    a contact point disposed at the end of one or more or said extensions configured to contact the recipient's ear canal.

10. The device of claim 8, wherein said one or more vibration extensions are configured to contact the recipient's ear canal only in the cartilaginous region.

11. A bone conduction device for enhancing the hearing of a recipient, comprising:
    a sound input element configured to receive an acoustic sound signal;
    an electronics module configured generate an electrical signal representing said acoustic sound signal;
    a transducer configured to generate mechanical forces representing said electrical signal for delivery to the recipient's bone;
    one or more recesses disposed around the circumference of said transducer and configured to allow fluidic access through the recipient's ear canal; and
    one or more vibration extensions mechanically coupled to said transducer and configured to be inserted into the ear canal of the recipient, and further configured to vibrate in order to transmit said mechanical forces generated from said transducer to the recipient's bone.

12. The device of claim 11, further comprising:
a retainer, coupled to said electronics module and said transducer, configured to be inserted into and retained by the recipient's conchal bowl.

13. The device of claim 12, wherein said retainer has disposed therein said electronics module.

14. A bone conduction device for enhancing the hearing of a recipient, comprising:
a sound input element configured to receive an acoustic sound signal;
an electronics module configured generate an electrical signal representing said acoustic sound signal;
a transducer configured to generate mechanical forces representing said electrical signal for delivery to the recipient's bone;
one or more non-vibrating support arms coupled to said transducer and configured to provide an opposing force when said one or more vibrating extensions are vibrated; and
one or more vibration extensions mechanically coupled to said transducer and configured to be inserted into the ear canal of the recipient, and further configured to vibrate in order to transmit said mechanical forces generated from said transducer to the recipient's bone.

15. The device of claim 14, wherein said one or more non-vibrating support arms are configured to be radially flexible.

16. The device of claim 14, wherein said one or more vibration extensions are configured to contact the ear canal only in the cartilaginous region of the recipient's ear canal.

17. A method for rehabilitating the hearing of a recipient with a bone conduction device having one or more vibration extensions, mechanically coupled to a transducer, and configured to be inserted into the ear canal of the recipient, comprising:
receiving an electrical signal representative of an acoustic sound signal;
generating mechanical forces representative of the received electrical signal;
contacting the ear canal of the recipient with the one or more vibration extensions, wherein said contacting the ear canal is at a point along the one or more vibration extensions before their respective ends; and
delivering said mechanical forces to the recipient's skull.

18. The method of claim 17, wherein said generated mechanical forces are generated using a piezoelectric elements.

19. The method of claim 17, wherein said contacting the ear canal is only in the cartilaginous region of the recipient's ear canal.

20. The method of claim 17, further comprising:
maintaining fluidic access through the recipient's ear canal.

* * * * *